United States Patent [19]

Notman

[11] 4,311,671
[45] Jan. 19, 1982

[54] SYNTHESIS REACTOR

[75] Inventor: Alan Notman, Norton, England

[73] Assignee: Imperial Chemical Industries Limited, London, England

[21] Appl. No.: 185,440

[22] Filed: Sep. 9, 1980

[30] Foreign Application Priority Data

Sep. 14, 1979 [GB] United Kingdom ............... 31877/79

[51] Int. Cl.³ ............................................. B01J 8/04
[52] U.S. Cl. .................................. 422/148; 422/194; 422/198; 422/191
[58] Field of Search ............... 422/191, 192, 194, 198, 422/200, 211, 218, 236, 148

[56] References Cited

U.S. PATENT DOCUMENTS

| | | | |
|---|---|---|---|
| 2,384,874 | 9/1945 | Barr | 422/191 X |
| 3,353,924 | 11/1967 | Riopelle | 422/191 |
| 3,433,600 | 3/1969 | Christensen et al. | 422/191 |
| 3,433,609 | 3/1969 | Percival et al. | |
| 3,498,756 | 3/1970 | Carson | 422/191 |
| 3,697,416 | 10/1972 | Carson et al. | 422/191 X |
| 3,705,016 | 5/1972 | Ludwigsen et al. | 422/191 |
| 3,746,515 | 7/1973 | Friedman | 422/191 |
| 3,784,361 | 1/1974 | Kubec et al. | 422/191 X |

FOREIGN PATENT DOCUMENTS 1138827 6/1957 France .
2277035 6/1975 France .

Primary Examiner—William A. Cuchlinski, Jr.
Attorney, Agent, or Firm—Cushman, Darby & Cushman

[57] ABSTRACT

A reactor for catalytic gas reactions such as synthesis of methanol or ammonia comprises at least one cylindrical catalyst bed having a height not greater than half its over-all diameter and defined on its underside by a grid supported by a dished plate having peripheral mechanical connection to a downward extension of the bed wall. Preferably there are several such beds and an indirect heat exchanger upsteam of the downstream-most bed. The reactor is suitably 5–10 m in diameter and is especially for use at under 120 bar abs in an integrated process for producing methanol and ammonia.

10 Claims, 5 Drawing Figures

SYNTHESIS REACTOR

This invention relates to a synthesis reactor and to exothermic catalytic gas-phase processes using it, especially the synthesis of ammonia or methanol.

In an exothermic catalytic process it is necessary to control the temperature in order to avoid unfavourable reaction equilibria, catalyst damage and side reactions, which may occur if the temperature becomes too high. This has been effected on an industrial scale by three general methods, namely (a) having heat exchange surfaces within a catalyst bed, (b) allowing adiabatic reaction and then removing heat by indirect heat exchange and (c) allowing adiabatic reaction and then lowering the temperature by mixing cooler gas into the reacted gas. Method (c) is simple and has been used in recent large synthesis plants. In particular a reactor much used, especially for methanol synthesis, is described in U.K. Pat. No. 1,105,614.

We have realised that, although the intra-bed sparger arrangements described in U.K. 1,105,614 is suitable for plants having a moderate output such as up to 1500 metric tons per day, it is subject to drawbacks when the output is to be still higher. In particular, when the pressure is relatively low and the catalyst volume correspondingly large, the catalyst bed diameter required is too large for such sparging to be convenient, owing to the great number of spargers needed to effect good gas mixing over the whole area of the bed. If gas mixing zones between separated catalyst beds are used as an alternative, then it is necessary to keep the pressure drop uniform over the area of each bed, and it becomes difficult to support the catalyst-bearing grids over their whole area. A multi-bed quench reactor described in U.K. Pat. No. 1,153,255 does not provide for these special requirements of low pressure operation.

According to the invention a reactor for catalytic gas reactions comprises at least one catalyst bed in the form exteriorly of a cylinder having a vertical axis and a height not greater than half its over-all diameter, the bed being defined on its underside by a substantially flat grid supported by a dished plate having peripheral mechanical connection to a downward extension of the cylinder walls.

The cylinder can be part of the external shell of the reactor if it is to be operated at pressures and temperatures such that a "hot-wall" vessel can be used. Examples of processes for which such a reactor is suitable are methanol synthesis at under 120 bar pressure, under 300° C., and also low-pressure ammonia synthesis processes. For processes at higher pressures and temperatures, for example methanol synthesis over a zinc-chrome catalyst or ammonia synthesis especially at over 120 bar pressure, the cylinder is preferably part of an internal shell, known as a "cartridge", which is separated from an external pressure-resisting shell by a space through which relatively cold gas is circulated in order to keep the temperature of the outer shell down to a level that is safe at the operating pressure.

Each dished plate is preferably convex upwards. This means that the distance between the plate and the grid is relatively large at the periphery of the cylinder, so that it is convenient to provide a port giving access to the space between the plate and the grid. Such a port can accommodate a thermocouple or afford ventilation during catalyst charging or discharging.

Each grid is supported suitably by way of radial webs. Each plate preferably has a gas tight connection with the cylinder walls. If a downward gas flow passage from the space between the grid and the plate is required, the plate can be formed with a central hole; since gas flows centripetally from the space to this passage, the flow rate is this passage is rapid and thus preferably there is disposed in or near this passage a cooling means. If this cooling means is a gas inlet, such as a quench gas sparger, there is achieved very effective gas mixing and thus temperature control. Alternatively an indirect heat exchanger can be disposed in this passage. Such gas inlet sparger or heat exchanger is alternative or additional to any that may be disposed in the space between the grid and the disc.

The reactor preferably includes a plurality of the catalyst beds disposed one above the other. Then colder gas fed through the inlet sparger very effectively decreases the temperature of the gas leaving a bed to the inlet temperature of the next lower bed. After the downstream-most bed of such a plurality the reactor may contain a heat exchanger by which incoming colder gas is preheated to the inlet temperature of the first bed of the plurality. An especially useful reactor contains also, downstream of such a heat exchanger, a further catalyst bed. Since the reactants have already reacted to a large extent in the preceding beds, the temperature rise in an exothermic reaction in such a further bed is not large, and thus it can be operated adiabatically and can be of large volume so as to effect useful further conversion of the reactants. In a reactor of this type the volumes of the beds can be as follows, for example:

|  | | |
| --- | --- | --- |
|  | First | 1.0 |
|  | Second, after quench gas cooling of first bed effluent | 1.2–1.5 |
| (if present) | Third, after quench gas cooling of second bed effluent | 1.8–2.2 |
|  | Final, after cooling of third bed effluent in heat exchanger | 3.0–5.0 |

Any of the beds can be subdivided, if desired, as described below. A further advantage of the adiabatic bed following the heat exchanger is that all the gas leaving that bed can be passed to external heat recovery (for example steam superheating, steam generation or water heating), the heat required for reactants preheating to first bed inlet temperature having been supplied by the gas leaving the bed upstream of the heat exchanger.

The ratio of height to over-all diameter can be for example as low as 0.1 for the first bed, more typically in the range 0.1 to 0.25. Usually all the beds upstream of the heat exchanger have such a ratio not greater than 0.5. It is normally convenient for those beds to be all of the same over-all diameter, and accordingly the height to diameter ratio is proportional to the bed volumes. The bed downstream of the heat exchanger is required to be as large as convenient and is normally deep enough not to require a flat supporting grid.

Any of the beds can be subdivided in order, for example to limit the weight of catalyst to be supported, or to decrease pressure drop thus permitting the catalyst to be present in smaller particles. Decrease in pressure drop is achieved suitably by arranging for parallel flow through two subdivisions of a particular bed. For this purpose the plate beneath each bed-subdivision has a gas tight connection with the vessel walls, the first bed-subdivision is formed with at least one by-pass pipe leading through its grid and plate into the next subdivision and the second bed-subdivision is formed with a by-pass pipe leading gas from the outlet of the first subdivision to the outlet of the second subdivision, where the outlet gases of the two subdivisions are reunited. More than two subdivisions can be provided, but at the cost of some complexity in piping.

Using a plurality of beds the simple catalyst discharging procedure of reactors using a single catalyst bed with caged spargers as in U.K. 1,105,614 is of course not possible. However, the long life of catalysts now available for methanol synthesis or ammonia synthesis means that catalyst changing takes place relatively infrequently, and consequently the lengthier procedure of man-handling the catalyst down through discharge pipes from bed to bed is less objectionable.

The reactor shell is fabricated preferably by uniting a set of units by butt welds only. The units include upper and lower dished ends, which may be hemispherical and are normally fabricated by forging;

cylindrical sections, which may be fabricated by forging or more economically by rolling from plate and then welding;

profiled annular sections fabricated by forging and having upper and lower faces butt-weldable to the cylindrical sections and an inward annular face butt-weldable to the dished plates described next;

dished circular plates each having a circumferential face butt-weldable to the inward annular face, preferably formed with a central hole. These plates are suitably in the shape of segments of a hollow sphere. Each carries, welded-on or not, means such as radial webs for supporting a catalyst bed defining grid.

By the use of the profiled annular sections the connection of the load-bearing dished plates to the outer cylinder is by way of a forging, not a weld, and the butt welds are all inspectable; consequently the risk of cracking is decreased.

The above mode of construction makes it possible to build a reactor of large diameter, for example 5–10 meters, without the special equipment needed to forge a complete shell. It is particularly valuable for producing a hot-wall vessel for processes of methanol synthesis or ammonia synthesis at pressures under 120 bar abs. as described below. It can also be used for constructing a cartridge to be used inside a pressure-resisting outer shell.

In a methanol synthesis process characterised by the use of a synthesis reactor according to the invention the pressure is suitably in the range 30 to 120 bar abs. and more conveniently in the range 40 to 100 bar abs. The temperature is suitably in the range 160°–300° C., with a catalyst bed outlet temperature preferably in the range 240°–290° C., but lower by 5°–20° C. at the outlet of the final bed than at the outlet of the bed preceding the heat exchanger. Such temperatures provide for an acceptable methanol output rate (owing to favourable equilibrium) without producing the greater content of impurities that would result from operation at higher temperatures. The quench gas fed in through the spargers between the catalyst beds can be at under 50° C., but thermal efficiency is better if its temperature is in the range 50° to 200° C., because such temperatures can be reached by heat exchange between cold gas and reacted gas from which an external heat recovery has been taken, and because a relatively small heat exchanger is sufficient to heat from such a temperature to catalyst inlet temperature the portion (suitably 30–60% of the total) of the gas that is fed to the first bed. The gas leaving the last bed is preferably all passed to external heat recovery, especially by water heating. In this respect the process differs from that of U.K. Pat. No. 1,484,366 in which the reacted gas is passed through a feed gas preheater and a water heater in parallel.

The methanol content of the reacted gas leaving the final bed of the reactor is suitably in the range 2–7% $^v/v$ for a process at 60 bar abs and proportionately more at higher pressures. The volume space velocity through the total catalyst is suitably in the range 5000–50,000 hour$^{-1}$. The gas passed over the catalyst is normally a mixture of fresh synthesis gas and unreacted gas recycled from methanol recovery by cooling, condensation and separation.

The catalyst for methanol synthesis contains copper and usually also zinc oxide and one or more further oxides such as of chromium (our U.K. Pat. No. 1,010,871) or elements from Groups III–IV of the Periodic Table, especially aluminum (our U.K Pat. No. 1,159,035) or possibly manganese, vanadium, boron and rare earth metals.

The methanol synthesis gas as passed over the catalyst contains hydrogen and carbon monoxide and preferably also, to the extent of 1–20 especially 3–12% $^v/v$, carbon dioxide. The hydrogen content is preferably at least sufficient to convert all the carbon oxides to methanol but may possibly be as little as half this quantity or, more usefully, substantially greater, for example in the range 1.4 to 10 times this quantity. Such high hydrogen contents occure in a recycle process in which the fresh synthesis gas contains more than the stoichiometric quantity of hydrogen, for example when it has been made by steam reforming a hydrocarbon feed-stock containing more than 2 hydrogen atoms per carbon atom or by a process sequence involving carbon dioxide removal. Whichever reactant is in excess in the fresh synthesis gas, its concentration builds up as a result of recycle and is kept down to a design level by purging. In an important form of the invention the purged gas is passed to ammonia synthesis.

The methanol synthesis gas may contain non-reacting gases such as methane, nitrogen or noble gases. Like excess reactants, these also build up during a recycle process and their concentration is kept to a design limit by purging. The gas normally does not contain water vapour, although this would not be objectionable in quantities up to what would produce, by the shift reaction, the percentages of carbon dioxide set out above. Usually the percentage of carbon dioxide, present as such or as the result of shift reaction, is such as to produce a crude methanol containing 5–30% $^w/w$ of water.

If desired, the reactor can be used in a so-called "wet" methanol synthesis in which the starting gas contains steam (steam to dry gas ratio 0.1 to 0.3 by volume) in addition to the carbon dioxide already mentioned. Such a process is useful when it is desired to decrease to the maximum extent the carbon monoxide content of the unreacted gas after separation of methanol and water from it.

In an ammonia synthesis process characterised by the use of a synthesis reactor according to the invention the pressure can be at any of the levels in common use, for example in the range 120 to 500 bar abs., but is preferably in the range 30 to 120 bar abs. as a result of the large catalyst volume that can be provided relatively inexpensively by the reactor, especially if it is of the hot-wall type.

The catalyst used is the ammonia synthesis can be of the usual composition, namely iron with promoting quantities of non-reducible oxides such as those of potassium, calcium, aluminum and others such as of beryllium, cerium or silicon. In order to afford maximum activity and thus to compensate for the lower rate of reaction due to low pressure, the iron catalyst may contain also cobalt, suitably to the extent of 1-20% $^w$/w calculated as $Co_3O_4$ on the total oxidic composition from which the catalyst is made by reduction and in which the iron oxide is assumed to be all $Fe_3O_4$. The outlet temperature of the synthesis catalyst is preferably in the range up to 500° C., especially 350°-450° C. This is lower than has been usual, in order to obtain a more favourable synthesis equilibrium. The catalyst volume is suitable in the range 100-200 m$^3$ per 1000 metric tons per day output giving an ammonia outlet concentration in the range 8 to 18% $^v$/v, 2 to 5% $^v$/v of the ammonia being produced in the last bed. The ratio of recycled gas to fresh gas is suitable in the range 4 to 6.

After leaving the reactor the reacted synthesis gas is cooled, suitably with one or more heat recoveries, and ammonia is separated from it. Preferably cooling is finally to $-3°$ to $-10°$ C., to give anhydrous liquid ammonia, and the gas recycled contain 3 to 6% $^v$/v of ammonia. Part of the unreacted gas is purged, treated to recover ammonia from it and then preferably treated, for example, cryogenically or by adsorption, to separate a hydrogen rich stream and a stream containing noble gases, methane and any excess nitrogen.

In such a process the quench gas fed in through the spargers between the catalyst beds can be at under 50° C., but thermal efficiency is better if its temperature is higher, especially in the range 150°-300° C., because such temperatures can be reached by heat exchange between cold gas and reacted gas from which an external heat recovery has been taken and because a relatively small heat exchanger is sufficient to heat from such a temperature to catalyst inlet temperature the portion of the gas that is fed to the first bed. The gas leaving the last bed is subjected to external heat recovery, preferably by water heating or possibly by steam raising or steam superheating, and then to heat exchange with cold gas to produce the above-mentioned quench gas.

A particular application of the invention is to a process for producing methanol and ammonia which comprises the steps (a) generating a synthesis gas containing carbon oxides, nitrogen, hydrogen and small proportions of noble gases and methane;

(b) reacting the synthesis gas over a copper-containing methanol synthesis catalyst whereby to convert the carbon oxides and hydrogen incompletely to methanol;

(c) separating the methanol and passing the unreacted gas to a catalytic ammonia synthesis;

and is characterised by using a reactor as herein defined for at least one of the synthesis steps.

A number of ways of carrying out such a process have been described. The preferred way, as described in our co-pending U.K. application 7843955, filed on Nov. 10, 1978, is characterised by carrying out step (b) in two stages, the first in the substantial absence of initially present water vapour and the second in the presence of sufficient water vapour to convert to carbon dioxide substantially all the carbon monoxide not converted to methanol.

After the second part of step (b) an aqueous methanol condensate is recovered and the carbon dioxide is removed by known means.

The synthesis gas for methanol synthesis or ammonia synthesis or the combination process can be made by any suitable gasification process, for example non-catalytic partial oxidation of coal, residual hydrocarbon or vaporisable hydrocarbon, catalytic partial oxidation of vaporisable hydrocarbon or catalytic steam reforming. Catalytic steam reforming for ammonia synthesis or the combination process is conveniently carried out in two stages (i) primary catalytically reforming a hydrocarbon feedstock with steam to give a gas containing carbon oxides, hydrogen and methane;

(ii) secondary catalytically reforming the gas from stage (i) by introducing air and bringing the mixture towards equilibrium, whereby to produce a gas containing nitrogen, carbon oxides, hydrogen and a decreased quantity of methane.

The partial oxidation processes produce initially a gas rich in carbon monoxide, which is to be reacted with steam to give the required hydrogen-containing synthesis gas, whether for methanol synthesis or ammonia synthesis or the combination process. The steam for such a steam reforming or CO-steam reaction preferably is provided at least partly by direct heat exchange with water heated by heat exchange with hot reacted synthesis gas leaving the last bed of the methanol synthesis reactor or ammonia synthesis reactor or both. As an alternative such hot water is fed to a boiler supplying steam to the steam reforming or CO-steam reaction. For the latter steam supply method the water should, of course, be of boiler feed quality, but for direct heat exchange process condensate, possibly after minor purification such as $CO_2$-removal, can be used.

By such boiler feed water heating or such heating of water for direct heat exchange it is possible to supply up to about 70% of the reactant steam requirement for synthesis gas generation and 30–60% can be regarded as a convenient proportion. A process for producing methanol or ammonia or both at the pressures specified can, indeed, be designed to export high pressure or medium pressure steam, even after providing steam to power its own machines and for process feed.

Preferred reactors according to the invention is shown in the accompanying drawings, in which FIG. 1 is a sectional elevation of a "hot-wall" vessel;

Figure 1:
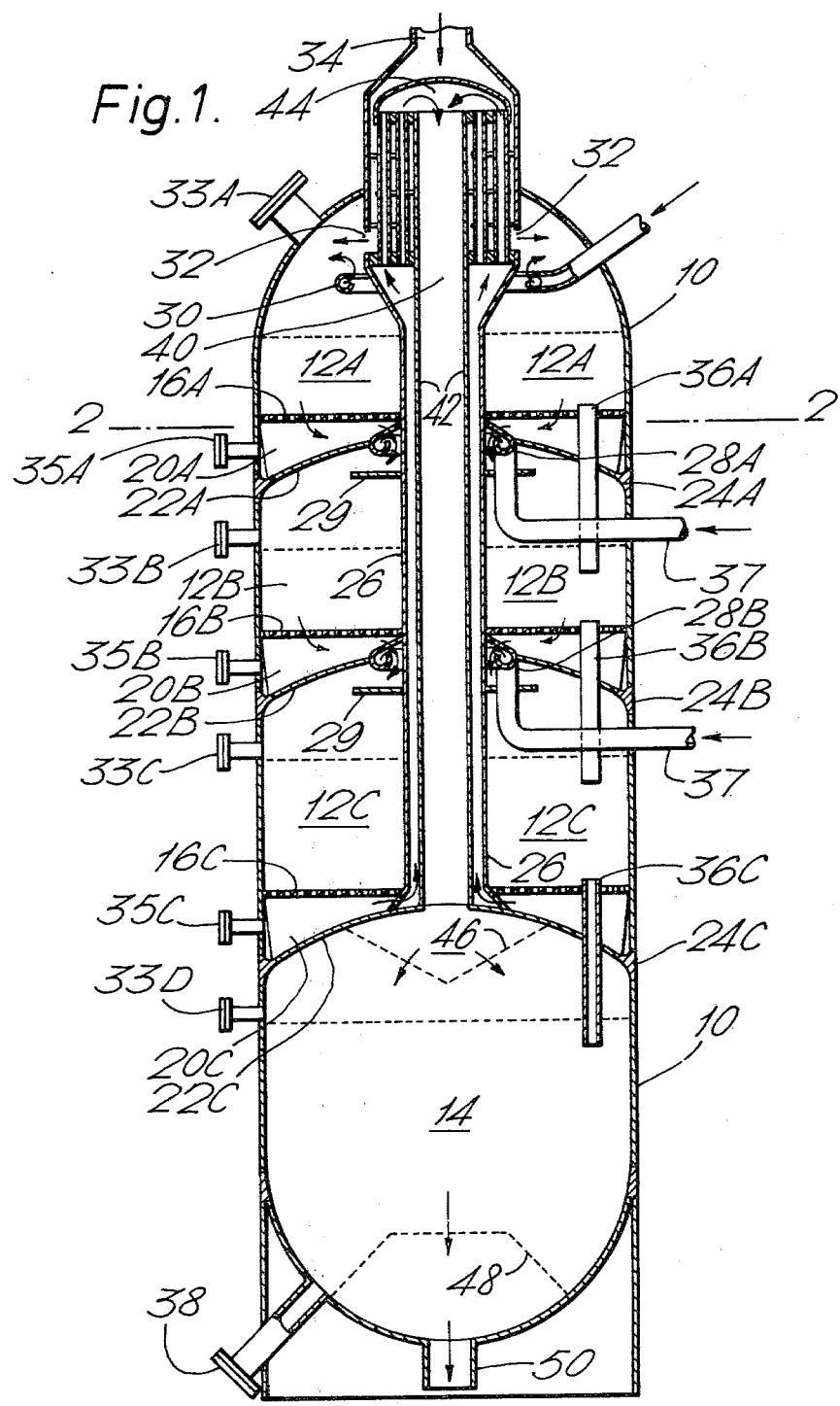

In FIG. 1, outer vessel 10 contains three small catalyst beds 12A, 12B and 12C and a large catalyst bed 14. Each small bed is bounded on its underside by a grid 16A, 16B, 16C respectively and when in use is normally charged with particulate catalyst up to the level shown by the dotted line. Each grid 16A, 16B, 16C is supported via radial webs 20A, 20B, 20C respectively by convex upward dished plates 22A, 22B, 22C respectively, each of which is secured to vessel 10 at 24A, 24B, 24C respectively, by means explained more fully with respect to FIG. 3 below. Each web 20A, 20B, 20C can at its inner end be welded to axial tube 26 to permit the weight of tube 26 and heat exchanger 40 above it to be carried by dished plates 22A, 22B, 22C. There is at the centre of each dished plate 22A, 22B, 22C a hole concentric with the axis of tube 26 but large enough in diameter to leave an annular gap in which is disposed spargers 28A and 28B each having perforations feeding centripetally upwards. Above catalyst bed 12A there is a sparger 30 adjacent feed holes 32 through which gas enters from main feed 34 via the cold side of heat exchanger 40. Each catalyst bed 12A, 12B, 12C is equipped with a thermocouple port 33A, 33B, 33C. Of these 33A is a manhole by which access is provided to the reactor interior by way of ladders and internal manholes (not shown) and 33B and 33C are additionally useful to provide ventilation when charging or discharging catalyst. Large catalyst bed 14 has a similar thermocouple port 33D. The space between each grid 16 and the dished plate beneath it is equipped with a thermocouple port 35A, 35B, 35C also useful to provide ventilation. Each catalyst bed 12 has a catalyst emptying pipe 36A, 36B, 36C, each passing through the dished plate beneath and finally feeding discharged catalyst into bed 14, which in turn is discharged externally (when required) through port 38. These emptying pipes are not closed at their upper ends because the pressure drop through them when filled with catalyst is greater than the pressure drop through grids 16A, 16B, 16C. The catalyst in bed 14 is supported on outlet grid 48 leading to reacted gas outlet 50.

Tube 26 supports at its upper end part of the weight of heat exchanger 40. Within tube 26 is disposed inner axial tube 42, such that the annular space between tubes 42 and 26 constitutes the inlet to the tubes of heat exchanger 40. The tubes of heat exchanger 40 are disposed in an annulus about inner axial tube 42; they discharge into plenum 44 and thus via inner tube 42 to distributor 46 at the inlet of large catalyst bed 14.

Figure 2:
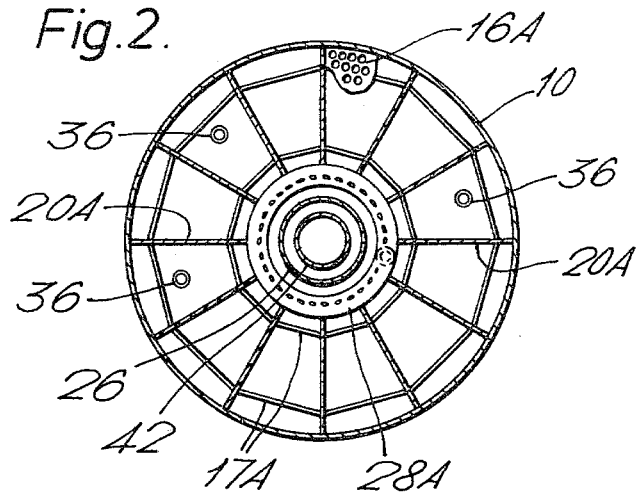
FIG. 2 is a sectional plan taken on the line 2—2.

In FIG. 2 the outer end of each of the 12 radial webs 20A is near but not in contact with the inner wall of reactor 10. The inner end of each radial web 20A is, at the level at which the section 2—2 is taken, near the inner extremity of dished plate 22A shown in FIG. 1 and also in FIG. 3 below. At its uppermost side, the inner end of each web is near or at the outer wall of outer axial tube 26 and thus supports catalyst grid 16A over substantially all its radial width. Support for catalyst grid 16A between webs 20A is provided by chordal bridging pieces 17A, two between each successive pair of webs. Inside the inner extremity of dished plate 22A is disposed sparger 28A, the gas outlet holes of which point centripetally upward. Inside the perforated ring of sparger 28A is the annular gap through which gas flows from the space between grid 16A and plate 22A into the space above catalyst bed 12B.

The above principles of construction are applicable also to a "cartridge" to be used inside a pressure resisting shell.

Figure 3:
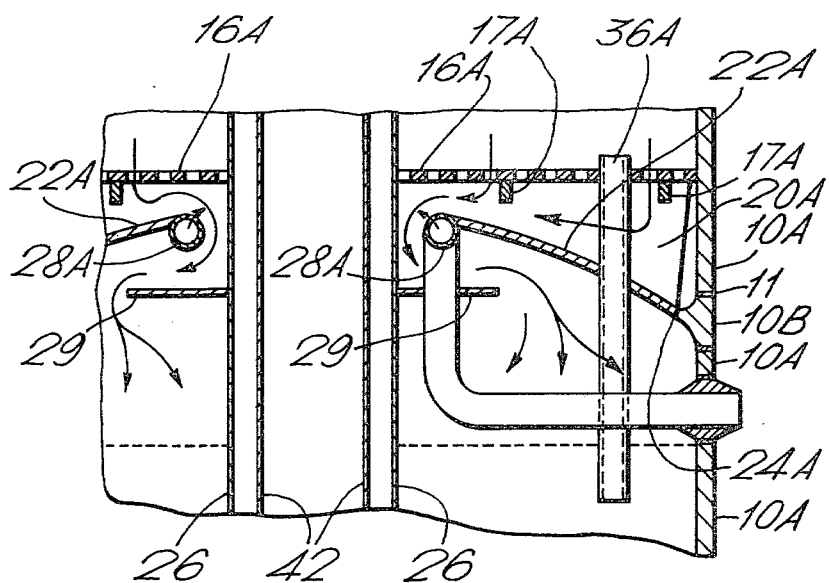
FIG. 3 is an enlarged sectional plan showing more clearly the mechanical construction of the reactor and the gas flow path between catalyst beds.

The mechanical construction shown in FIG. 3 can be used especially for a "hot-wall" vessel, that is, one in which the outer wall shown is the pressure-resisting shell. Outer vessel 10 includes rolled welded cylindrical sections 10A and forged profiled annular sections 10B. These are fabricated separately and joined together at butt welds 11. Dished plates 22A are likewise fabricated separately and are welded to profiled sections at 24A. Webs 20A are welded to the upper surface of plates 22A. The construction of the dished plates 22B and 22C supporting grids 16B and 16C, respectively, is similar. The upper and lower dished ends shown in FIG. 1 are likewise forged separately and welded to cylindrical sections 10A. Thermocouple ports 33A and 35A and quench inlets ports 37 can be fabricated into cylindrical sections 10A before assembly of the wall sections. By the use of this mechanical construction there need be no welded joint between the outer wall and a load-bearing member at an angle to the wall and, as a result, the uncertainty involved in making such joints strong enough can be avoided. If vessel 10 is a cartridge and is not required to withstand high internal pressure, plates 22A can be welded directly to the vessel inner wall.

In order to show the gas flow path more clearly, the inner edge of webs 20A and the circumference of spargers 36 have been omitted. The arrows show that the gas is forced centripetally into the annular gap, at the entrance to which it meets and mixes thoroughly with gas fed through sparger 36. The mixed gas then passes outwardly beneath plate 22A and is directed over the upper surface of catalyst 12B by means of baffle 29.

Figure 4:
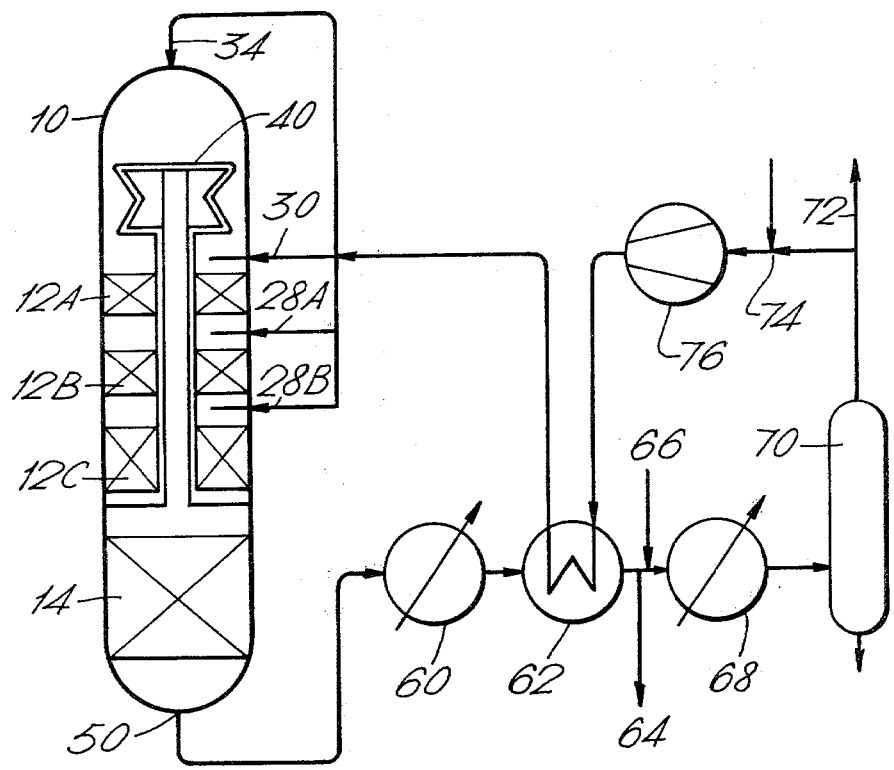
FIG. 4 is a flow diagram showing external flow connections to the reactor.

In FIG. 4 reactor 10 is represented with sufficient detail to show the gas flow paths but not the mechanical construction. The gas entering by main gas inlet 34 is heated to slightly above catalyst inlet temperature in the space surrounding the tubes of heat exchanger 40. Its temperature is regulated by colder gas fed in through sparger 30, whereafter it enters catalyst bed 12A and reacts exothermally. The gas temperature is lowered by colder gas fed in through sparger 28A, whereafter the mixed gas enters catalyst bed 12B and reacts exothermally. There is a third stage cooling, by gas fed in through sparger 28B, and a third stage of reaction, in bed 12C. The hot gas then passes upwards and into the tubes of heat exchanger 40, is cooled therein and then passes into catalyst bed 14 where it undergoes further reaction. The reacted hot gas leaving reactor 10 at 50 is all passed into external heat recovery heat exchanger 60 which is one or more of a water heater, boiler and steam superheater. The resulting cooled gas is cooled further at 62 in heat exchange with unreacted cold gas, which thereby is heated to the "colder" temperature at which it is fed to reactor 10 at points 34, 30, 28A and 28B. A minor stream of the cooled reacted gas may be purged off at 64 if desired and in this event a feed of fresh synthesis gas can be made at 66. These positions for purge and feed are preferred if the fresh synthesis gas contains impurities and these are to be removed with the product. The cooled reacted gas is cooled further at 68 to below the dewpoint of the product and the product is separated in catchpot 70 which unreacted gas passes overhead. A purge stream may be taken at 72 and fresh synthesis gas added at 74 if this has not been done at positions 64 and 66. The gas is then recycled via circulator 76, reheated to "colder" temperature at 62 and passed to the feed points of reactor 10.

Figure 5:
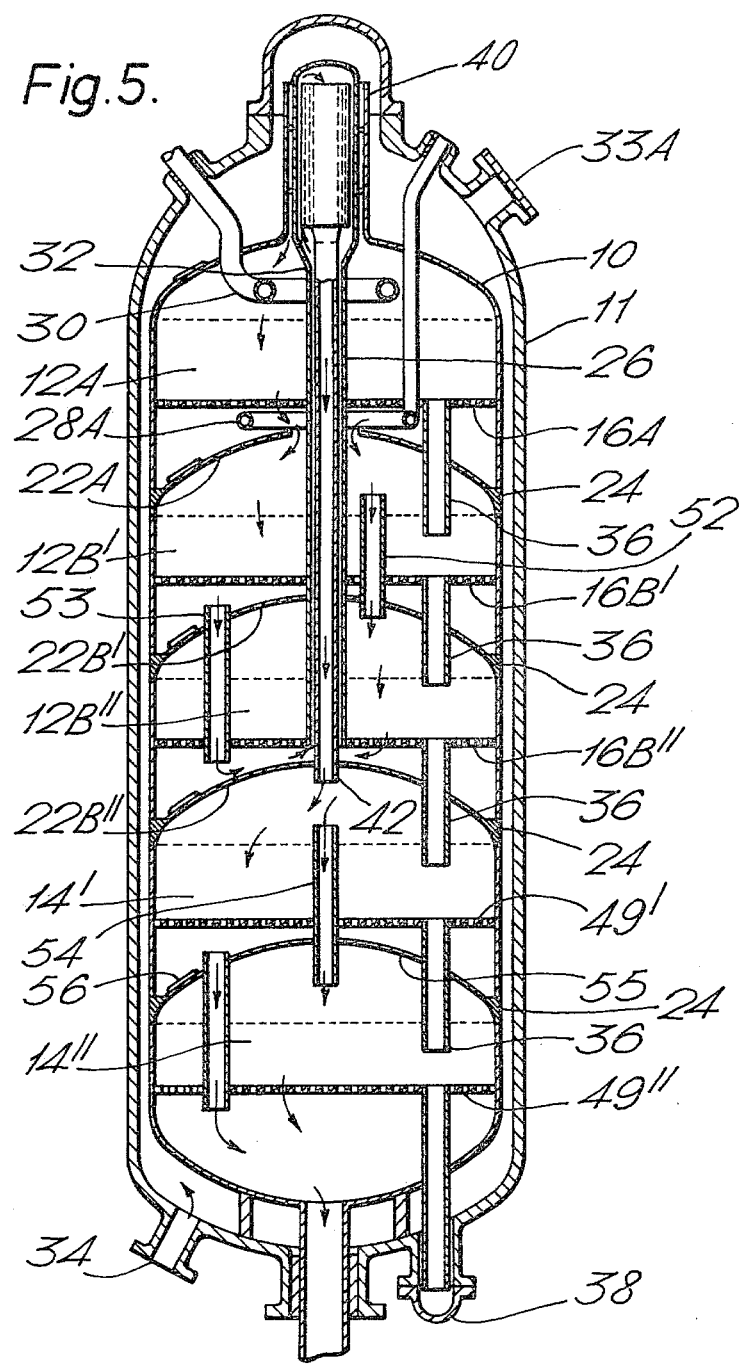
FIG. 5 is a sectional elevation of a cartridge-type reactor.

In FIG. 5 cartridge 10 is supported within pressure-resisting shell 11. It contains two small catalyst beds and one large catalyst bed, but the second small bed and the large bed are each subdivided. The mechanical construction of the bed subdivisions is the same as of beds 12A, 12B, 12C and 14 in FIG. 1 and has not been shown in detail. First bed 12A is fed by sparger 30 near to feed holes 32 at the outlet of the cold side of heat exchanger 40, which receives gas which has entered by main feed 34 and warmed by passage through the space between cartridge 10 and shell 11. Gas leaving bed 12A through grid 16 mixes with colder gas fed in through sparger 28A and passes through the central hole in plate 22A into the space above the first subdivision 12B¹ of the second catalyst bed 12B. From this space part of the gas flows through subdivision 12B¹ but the rest flows through by-pass pipe 52 leading past grid 16B¹ and plate 22B¹ into space above 12B¹¹. A second by-pass pipe 53 is provided between the space below grid 16B¹ and above plate 22B¹ to carry gas leaving subdivision 12B¹ to the space beneath subdivision 12B¹¹. Thus, unlike plate 22A, plate 22B has no central hole and is connected gas-tightly to axial tube 26. Gases from by-pass pipe 53 and from subdivision 12B¹¹ unite in the space between grid 16B¹¹ and plate 22B¹¹ and are fed to the hot side of heat exchanger 40 via the space between axial tubes 26 and 42.

Gas cooled in heat exchanger 40 returns through axial tube 42 into the space above first subdivision 14¹ of bed 14. Part of it flows through subdivision 14¹ but the rest flows through by-pass pipe 54 leading past grid 49¹ and plate 55 into the space above second subdivision 14¹¹. A second by-pass pipe 56 is provided between the space below grid 49¹ and above plate 55 to carry gas leaving subdivision 14¹ to the space beneath subdivision 14¹¹. Gases from by-pass pipe 56 and from subdivision 14¹¹ unite in the space beneath grid 49¹¹ and leave the vessel via outlet 50.

The external connections of this vessel can be as in FIG. 4.

In a methanol synthesis process according to the invention the gas temperature, pressure, composition and flow rate are, for example, as set out in Table 1.

ties. The purge gas taken at 72 is passed to ammonia synthesis, by way of known purification steps.

Table 2 shows representative data for an ammonia synthesis process according to the invention.

TABLE 2

| Position | Temp °C. | Pressure bar abs | Gas composition % v/v | | | | | Flow rate kg mol h⁻¹ |
| --- | --- | --- | --- | --- | --- | --- | --- | --- |
| | | | NH₃ | H₂ | N₂ | CH₄ | Ar | |
| 34, 30, 28A, 28B and space between cartridge and shell | 250 | 108 | 3.79 | 65.58 | 22.19 | 6.95 | 1.50 | 3100 (total) |
| 12C outlet | 456 | 106 | 12.0 | 58.9 | 19.9 | 7.5 | 1.6 | 2873 |
| 14 inlet | 377 | | | | | | | |
| 50 | 419 | 105 | 15.04 | 56.42 | 19.7 | 7.71 | 1.66 | 2797 |

As in the methanol synthesis the last bed (14) is operated at a lower outlet temperature than the preceding bed in order to increase the equilibrium ammonia content of the gas. All the exothermic heat evolved in the formation of the extra 3.04% of ammonia in bed 14 is available for external heat recovery. The gas at 419° C. is cooled in water heater 60° to 280° C. with recovery of heat at the rate of 3229 metric ton calories per hour, then cooled further in heat exchange at 62 with reactant gas, which becomes heated to 250° C. Cooler 68 is in two stages, in the first of which the gas is cooled to 23° C. by heat exchange with gas leaving catchpot 70 overhead, and in the second of which it is cooled to −6° C., at which ammonia condenses and is separated in catchpot 70. Purge gas taken at 72 is contacted with water to recover ammonia from it and passed to cryogenic fractionation, the hydrogen-enriched stream of which is returned to the synthesis, suitably at 74, at which fresh synthesis gas is also fed.

I claim:

1. A reactor for catalytic gas reactions comprising:
   a plurality of series connected catalyst beds, each disposed one above the other, in a reactant flow path;
   each said catalyst bed having an exterior cylindrical form with a vertical axis and a height not greater than its over-all diameter, and being defined on its underside by a substantially flat grid supported by

TABLE 1

| Position | Temp °C. | Press. bar abs | Gas composition % v/v | | | | | | | Flow rate, Kg mol h⁻¹ |
| --- | --- | --- | --- | --- | --- | --- | --- | --- | --- | --- |
| | | | CO | CO₂ | H₂ | CH₄ | N₂+A | CH₃OH | H₂O | |
| 34 | | | | | | | | | | 3463.0 |
| 30 | | | | | | | | | | 703.8 |
| 28A | 142 | 77.5 | 7.01 | 4.55 | 67.03 | 0.69 | 20.3 | 0.34 | 0.06 | 1711.0 |
| 28B | | | | | | | | | | 2296.8 |
| 12C outlet | 280 | 75.5 | 5.36 | 3.87 | 63.77 | 0.74 | 21.69 | 3.47 | 1.08 | 7622.5 |
| 50 | 270 | 75.0 | 4.19 | 3.92 | 63.04 | 0.75 | 22.12 | 4.82 | 1.13 | 7476.7 |
| 72 | 40 | 80.0 | | | | | | | | 761.8 |

The last bed (14) is operated at a lower outlet temperature than the preceding bed (12C) in order to increase the equilibrium methanol content of the gas. All the exothermic heat evolved in the formation of the extra 1.35% of methanol in bed 14 is available for external heat recovery. The gas at 270° C. is cooled in water heater 60° to 171° C. with recovery of heat at the rate of 5640 metric ton-calories per hour, then cooled to 108° C. in heat exchange at 62 with reactant gas, which becomes heated to 142° C. Final cooling at 68 is to 40° C. after which a crude methanol is separated at 70 containing 20% by mols of water and traces of volatile impuria dished plate having peripheral mechanical connection to a downward extension of the cylinder walls;
a heat exchanger disposed downstream, in the reactant flow path, of the downstream-most of said plurality of catalyst beds; and
a further catalyst bed disposed downstream, in the reactant flow path, of said heat exchanger.

2. A reactor according to claim 1 in which each dished plate is convex upwards.

3. A reactor according to claim 1 in which at least one of the catalyst beds is subdivided and at least two bed subdivisions are connected for parallel gas flow.

4. A reactor as recited in claim 1 wherein the cylinder includes in each catalyst bed a part of an external shell of the reactor, and wherein said reactor is capable of use in a process of methanol synthesis by reacting carbon dioxide with hydrogen at a pressure in the range of 30–120 bars absolute, and a temperature in the range of 160–300 degrees C over a copper-containing catalyst.

5. A reactor as recited in claim 1, wherein the cylinder included in each catalyst bed is part of an internal shell separated from an external pressureresisting shell by a space; and means for circulating relatively cold gas through said space; and wherein said reactor is capable of use in a process of ammonia synthesis by reacting nitrogen with hydrogen at a pressure in the range of 30–120 bars and a temperature in the range of 350–450 degrees C.

6. A reactor as recited in claim 1 wherein all of said beds upstream of said heat exchanger have a height to overall diameter ratio not greater than 0.5.

7. A reactor for catalytic gas reactions comprising at least first and second series connected—in a reactant flow path—catalyst beds, each having a predetermined volume;
   each said catalyst bed having an exterior cylindrical form with a vertical axis and a height not greater than its over-all diameter, and being defined on its underside by a substantially flat grid supported by a dished plate having peripheral mechanical connection to a downward extension of the cylinder walls;
   means for effecting quench gas cooling of effluent from said first catalyst bed before passing to said second bed;
   a heat exchanger disposed downstream, in the reactant flow path, of said second bed;
   a final catalyst bed disposed downstream, in the reactant flow path, of said heat exchanger; and
   the volumes of said catalyst beds being proportionately: first bed, 1.0; second bed, 1.2–1.5; final bed, 3.0–5.0.

8. A reactor according to claims 1 or 7 and having a diameter in the range 5–10 meters.

9. A reactor as recited in claim 8 comprising a set of units, and means for uniting said set of units into an integral structure, said means for uniting said set of units consisting of butt-welds.

10. A reactor as recited in claim 7 wherein said series connected catalyst beds comprise first, second, and third beds, said third bed having a proportionate volume of 1.8–2.2; and wherein said reactor further comprises means for effecting quench gas cooling of effluent from said second catalyst bed before passing into said third catalyst bed, said heat exchanger disposed downstream of said third catalyst bed.

* * * * *